(12) United States Patent
Liu

(10) Patent No.: US 9,316,475 B2
(45) Date of Patent: Apr. 19, 2016

(54) HEIGHT MEASUREMENT DEVICE

(71) Applicant: Chia-Hsin Liu, Taipei (TW)

(72) Inventor: Chia-Hsin Liu, Taipei (TW)

( * ) Notice: Subject to any disclaimer, the term of this patent is extended or adjusted under 35 U.S.C. 154(b) by 131 days.

(21) Appl. No.: 14/171,869

(22) Filed: Feb. 4, 2014

(65) Prior Publication Data
US 2015/0219432 A1  Aug. 6, 2015

(51) Int. Cl.
*G01B 5/06* (2006.01)
*A61B 5/107* (2006.01)

(52) U.S. Cl.
CPC .............. *G01B 5/061* (2013.01); *A61B 5/1072* (2013.01)

(58) Field of Classification Search
CPC .... A61B 5/1072; A61B 5/107; A61B 5/1076; G01B 3/04; G01B 3/06; G01B 11/0608; G01B 3/1084; G01B 5/061
USPC ..................... 33/512, 478, 485, 483
See application file for complete search history.

(56) References Cited

U.S. PATENT DOCUMENTS

| | | | | |
|---|---|---|---|---|
| 2,501,948 A | * | 3/1950 | Knipp ................................. | 33/8 |
| 2,736,100 A | * | 2/1956 | Landau ............................ | 33/512 |
| 3,066,419 A | * | 12/1962 | King ................................ | 33/342 |
| 4,134,212 A | * | 1/1979 | Allen ............................... | 33/512 |
| 4,495,702 A | * | 1/1985 | Bergstedt ........................ | 33/512 |
| 5,758,858 A | * | 6/1998 | Barnes ............................ | 248/544 |
| 5,904,142 A | * | 5/1999 | Policastro et al. ............. | 600/561 |
| 6,128,824 A | * | 10/2000 | Yang ................................ | 33/511 |
| 6,237,239 B1 | * | 5/2001 | Miyazaki ........................ | 33/512 |
| 8,528,221 B2 | * | 9/2013 | Glock, Jr. ........................ | 33/512 |
| 8,869,415 B1 | * | 10/2014 | Haykeen ......................... | 33/512 |
| 2005/0155246 A1 | * | 7/2005 | Montagnino ................... | 33/832 |
| 2010/0223799 A1 | * | 9/2010 | Dunham ......................... | 33/512 |
| 2011/0072677 A1 | * | 3/2011 | Hong ............................... | 33/832 |
| 2012/0144686 A1 | * | 6/2012 | Haykeen ......................... | 33/512 |
| 2013/0091718 A1 | * | 4/2013 | Haykeen ......................... | 33/512 |
| 2013/0160313 A1 | * | 6/2013 | Swanson ......................... | 33/430 |
| 2013/0338542 A1 | * | 12/2013 | Rathi ............................. | 600/595 |

* cited by examiner

*Primary Examiner* — Yaritza Guadalupe-McCall
(74) *Attorney, Agent, or Firm* — Muncy, Geissler, Olds & Lowe, P.C.

(57) ABSTRACT

A height measurement device, detachably disposed on an article, includes a body and a measurement unit. The body includes a clamping member, a height indicator, and a pivot member. The clamping member has a first joint portion and a clamping slit, wherein the clamping slit is capable of clamping the article. The height indicator has a first pivot portion. The pivot member has an adjacent portion and a second joint portion, and is pivotally jointed the height indicator to the clamping member through the first pivot portion, whereas the pivot member is moved to allow the second joint portion joint to the first joint portion, the adjacent portion abuts the height indicator onto the clamping member so as to fix the height indicator at a measurement position. The measurement unit disposed on the body is for use in measuring a height of the measurement position.

7 Claims, 13 Drawing Sheets

HEIGHT MEASUREMENT DEVICE

FIELD OF THE INVENTION

The present invention relates to a height measurement device, and in particular to a height measurement device that is composed of a body and a measurement unit.

BACKGROUND OF THE INVENTION

Conventionally, a user usually uses a height measurement device of floor type to measure height. The user stands on the height measurement device and receives a height value with a measuring process which was measured form the soles of the user's feet to the top of the user's head in 3 to 6 seconds. However, the volume of the height measurement device is large and the prize thereof is expensive, and most people do not have said measurement device at home. In order to measure the exact height, the user has to go to hospital or a place having the height measurement device, and sometimes it charges some fee to measure height. Thus, the said situation for measuring height wastes time and money. Moreover, the growth of children is considered by the parents. Therefore, there is a need to exactly measure the height with a height measurement device and reduce the volume thereof.

SUMMARY OF THE INVENTION

One aspect of the present invention is to provide a height measurement device that is composed of a body and a measurement unit to accurately measure height and has the characteristics of less volume and easy-carrying.

To achieve the above aspect, the present invention provides a height measurement device, detachably disposed on an article, including a body and a measurement unit. The body includes a clamping member, a height indicator and a pivot member. The clamping member has a first joint portion and a clamping slit, wherein the clamping slit is capable of clamping the article. The height indicator has a first pivot portion. The pivot member has an adjacent portion and a second joint portion, and is pivotally jointed the height indicator to the clamping member through the first pivot portion, whereas the pivot member is moved to allow the second joint portion joint to the first joint portion, the adjacent portion abuts the height indicator onto the clamping member so as to fix the height indicator at a measurement position. The measurement unit disposed on the body is for use in measuring a height of the measurement position.

According to the present invention, with a composition of the clamping member, the height indicator, the pivot member and the measurement unit, the height measurement device is portable and can be detachably disposed on an article such as doors or columns, then easily moved along the article so that a height of a user can precisely measured.

BRIEF DESCRIPTION OF THE DRAWINGS

The present invention will be apparent to those skilled in the art by reading the following description of preferred embodiments thereof with reference to the drawings, in which.

DETAILED DESCRIPTION OF THE PREFERRED EMBODIMENTS

Figure 1:
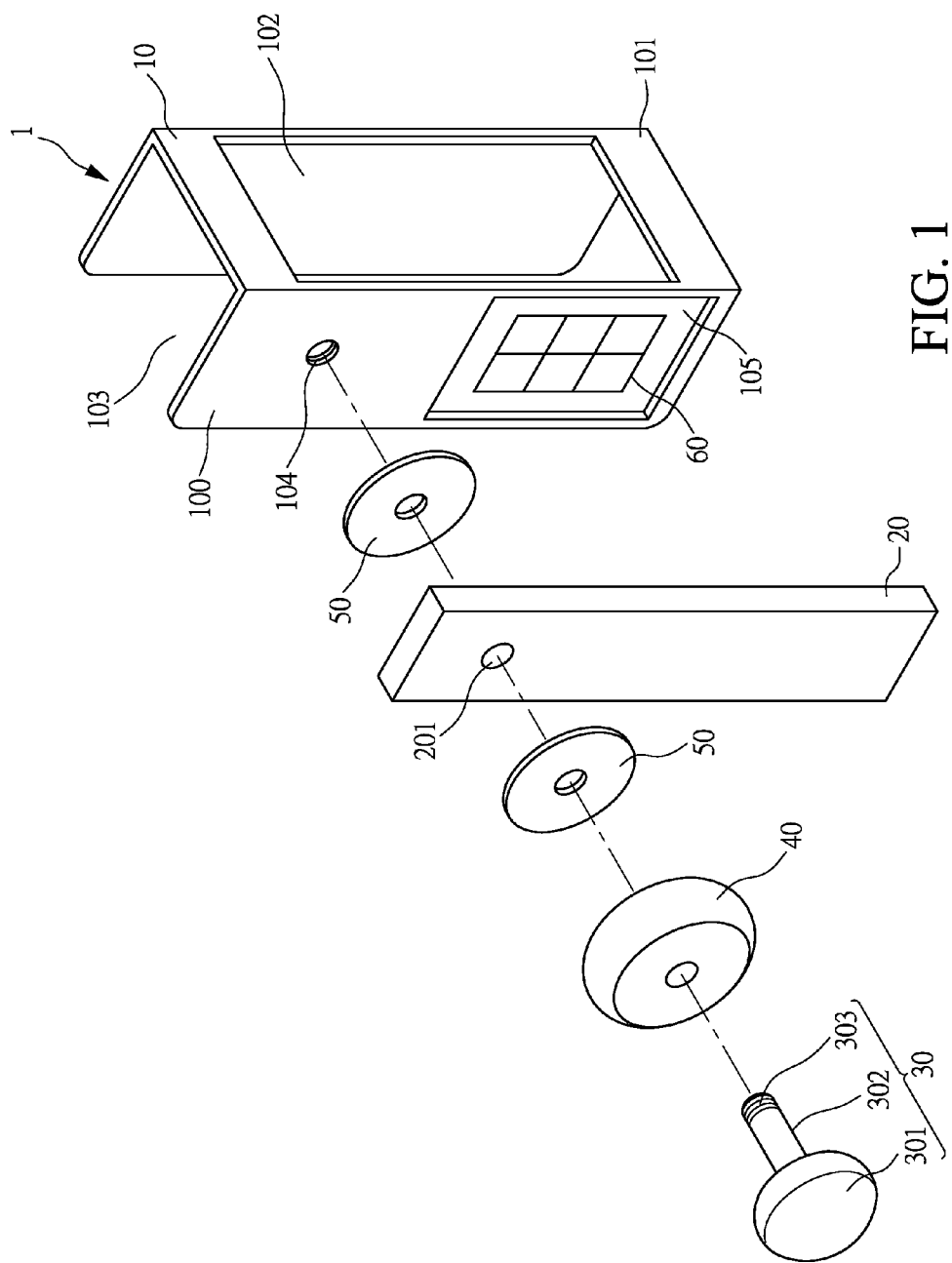
FIG. 1 is an exploded view of the height measurement device according to the first embodiment of the present invention.
Figure 2:
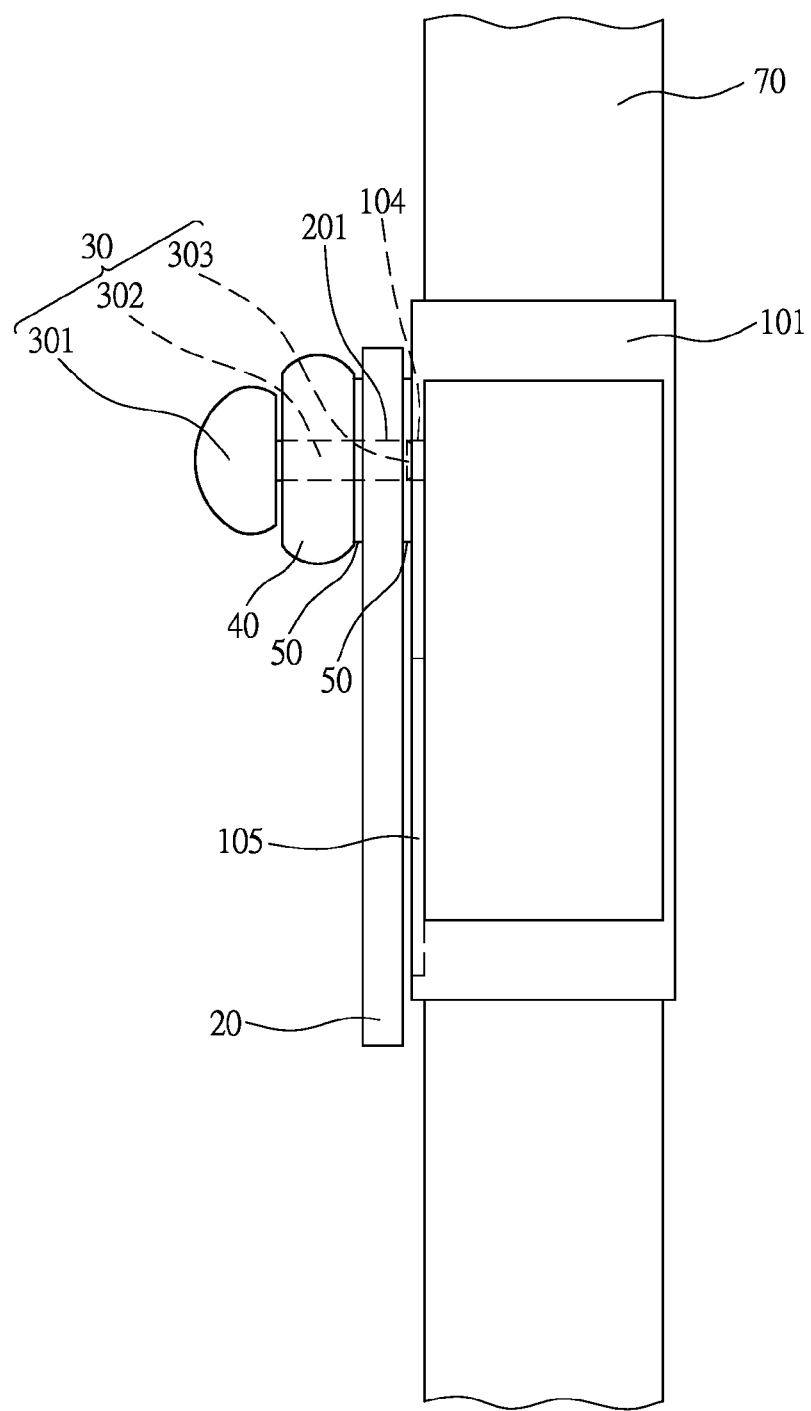
FIG. 2 a cross-sectional view of the height measurement device according to the first embodiment of the present invention.
Figure 3:
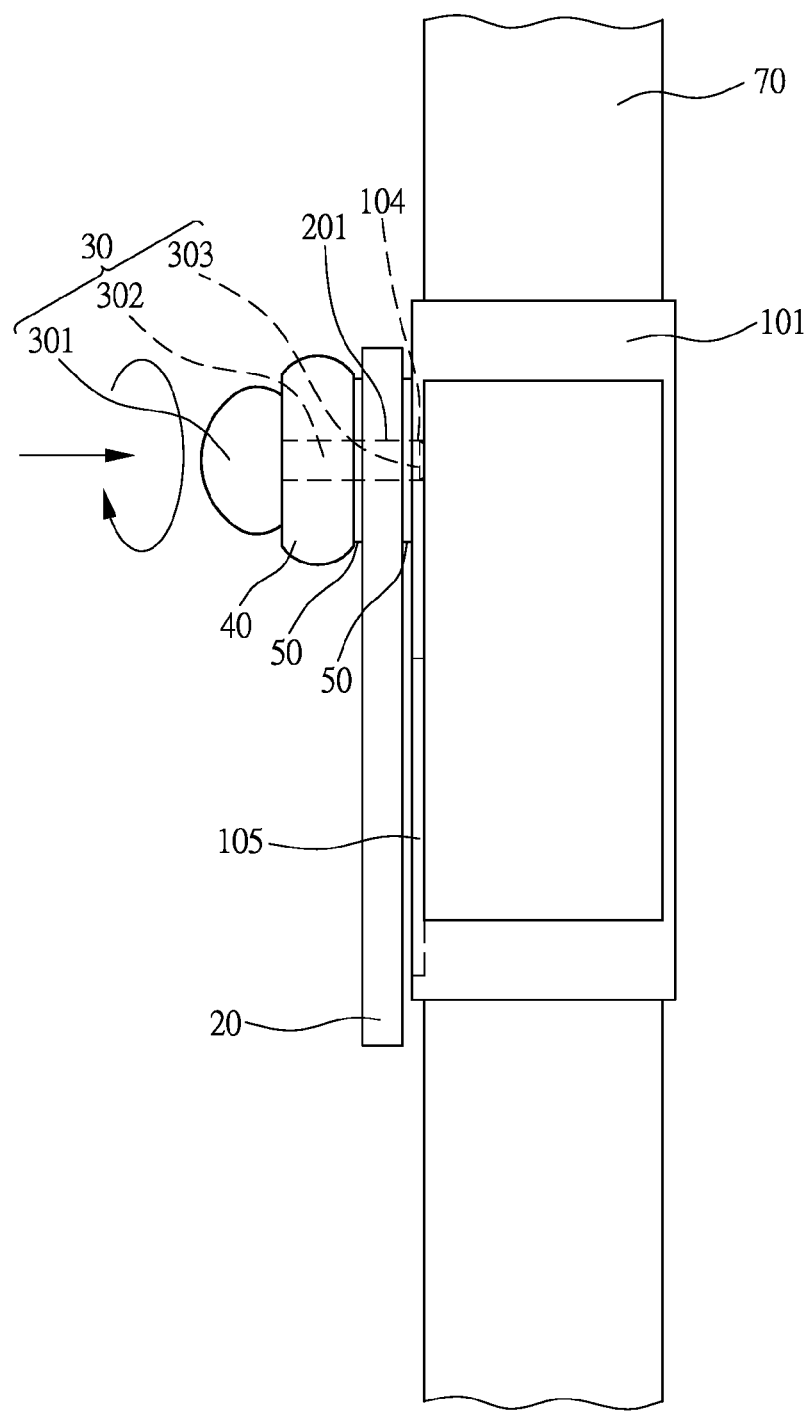
FIG. 3 a cross-sectional view of the height measurement device according to the first embodiment of the present invention.

FIG. 1 is an exploded view of the height measurement device according to the first embodiment of the present invention; FIG. 2 a cross-sectional view of the height measurement device according to the first embodiment of the present invention; FIG. 3 a cross-sectional view of the height measurement device according to the first embodiment of the present invention. With reference to the drawings and in particular to FIG. 1, the present invention is a height measurement device, which comprises a body 1 and a measurement unit 40. The body 1 comprises a clamping member 10, a height indicator 20, a pivot member 30, and a record 60, wherein the clamping member 10 is composed of a first side wall 100, a second side wall 101 and a thirty side wall 102 and forms a damping slit 103 thereof, the first side wall 100 has a first joint portion 104, the height indicator 20 has a first pivot portion 201. The pivot member 30 is pivot jointed to the height indicator 20 on the first side wall 100 and comprises an adjacent portion 301, a second pivot portion 302 and a second joint portion 303, wherein the second pivot portion 302 is jointed to the adjacent portion 301 with one end, and the other end of the second pivot portion 302 is jointed to the second joint portion 303. The second pivot portion 302 is pivot jointed to the first pivot portion 201, and the second joint portion 303 is moveable jointed to the first joint portion 104. While the pivot member 30 moves to a packing position, the adjacent portion 301 abuts the height indicator 20 whereby the height indicator 20 and the clamping member 10 are packed by the adjacent portion 301 (please refer to FIG. 2 and FIG. 3). The measurement unit 40 (the measurement unit 40 is a graduation measurement unit in this embodiment, such as a measuring tape) is disposed on the body.

The present invention is a height measurement device which further comprises two gaskets 50, one of the gaskets 50 is disposed between the damping member 10 and the height indicator 20, and the other one is disposed between the height indicator 20 and the adjacent portion 301. The clamping member 10 further comprises a second accommodating portion 105 on the first side wall 100, and the record list 60 is demountable in the second accommodating portion 105.

Figure 4:
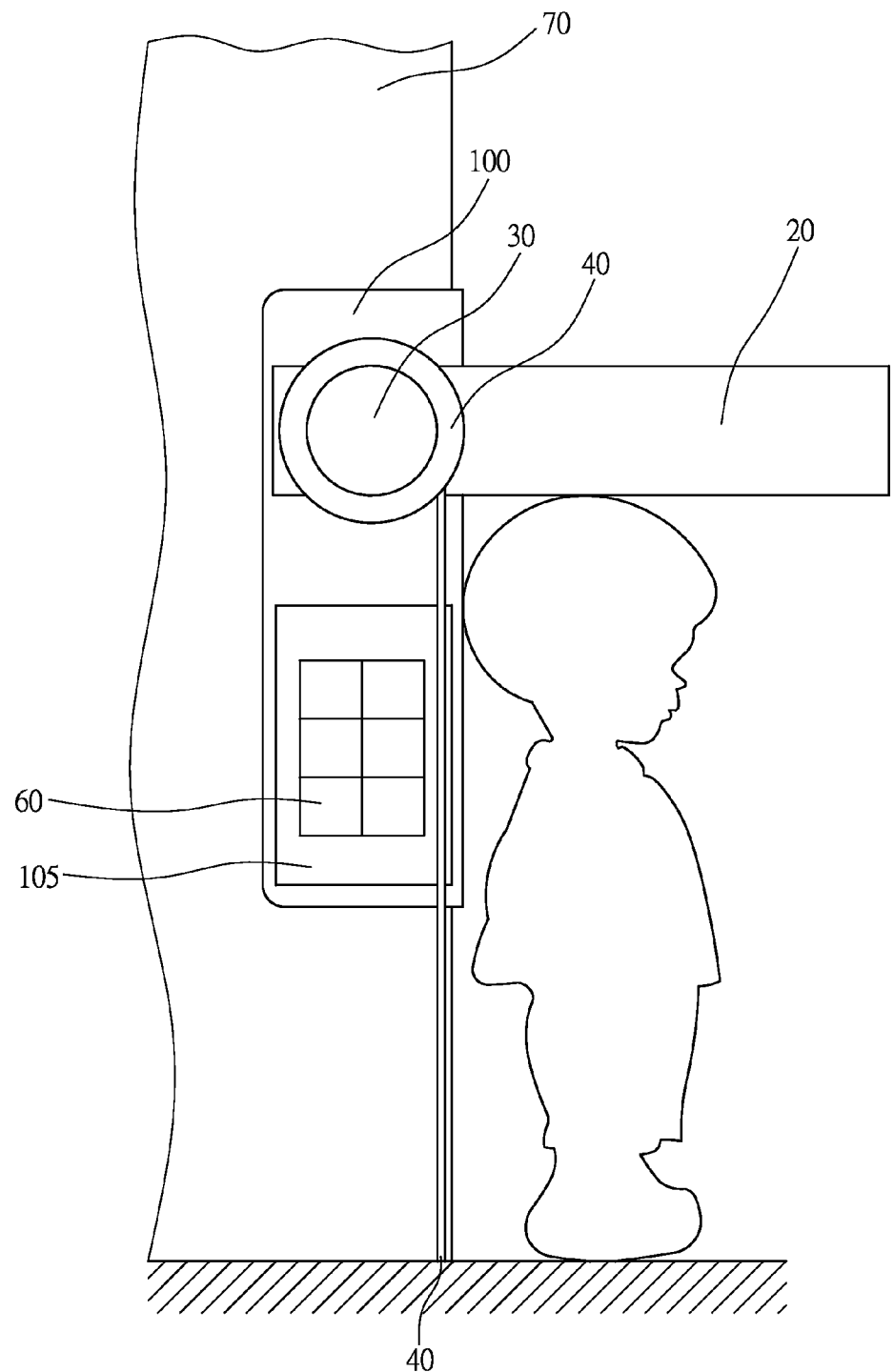
FIG. 4 is an operating schematic view of the height measurement device according to the first embodiment of the present invention.

FIG. 4 is a schematic view showing a use of the height measurement device according to the first embodiment of the present invention. With reference to the drawings and in particular to FIG. 4, the present invention is a height measurement device. First, the user takes the clamping member 10 to clamp a door plank 70 and turns around the height indicator 20 to a horizontal position, and the height indicator 20 is perpendicular to the second side wall 101. Then, the user adjusts the clamping member 10 to move up and down along the door plank 70. The user locks the pivot member 30 when the height indicator 20 abuts the top of the user's head, and rotates the pivot member 30 to a packing position. The adjacent portion 301 abuts the height indicator 20 whereby the height indicator 20 and the clamping member 10 are packed by the adjacent portion 30. The graduation tool of the measurement unit 40 is drawn to the floor for measuring height exactly, and the record list 60 is put in the accommodating portion 105 of the first side wall 100 to record the value of height every time.

Figure 5:
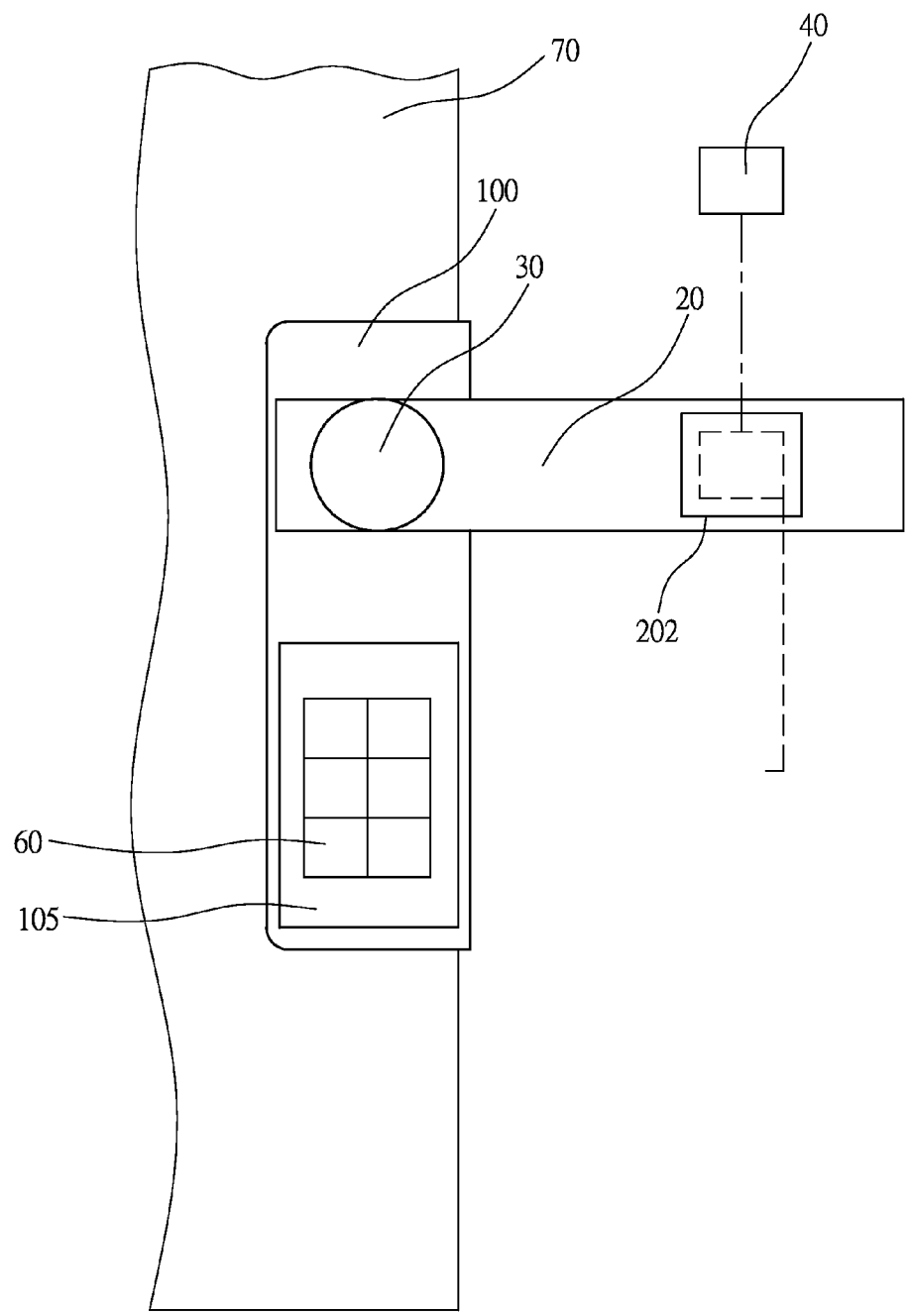
FIG. 5 is an operating schematic view of the height measurement device according to the second embodiment of the present invention.

FIG. 5 is a schematic view showing a use of the height measurement device according to the second embodiment of the present invention. With reference to the drawings and in particular to FIG. 5, the operation of the second embodiment as same as the first embodiment. However, the height indicator 20 comprises a second accommodating portion 202 whereby the measurement unit 40 is disposed therein, and the measurement unit 40 can be used in appropriate somewhere while removed from the accommodating portion 202.

Figure 6:
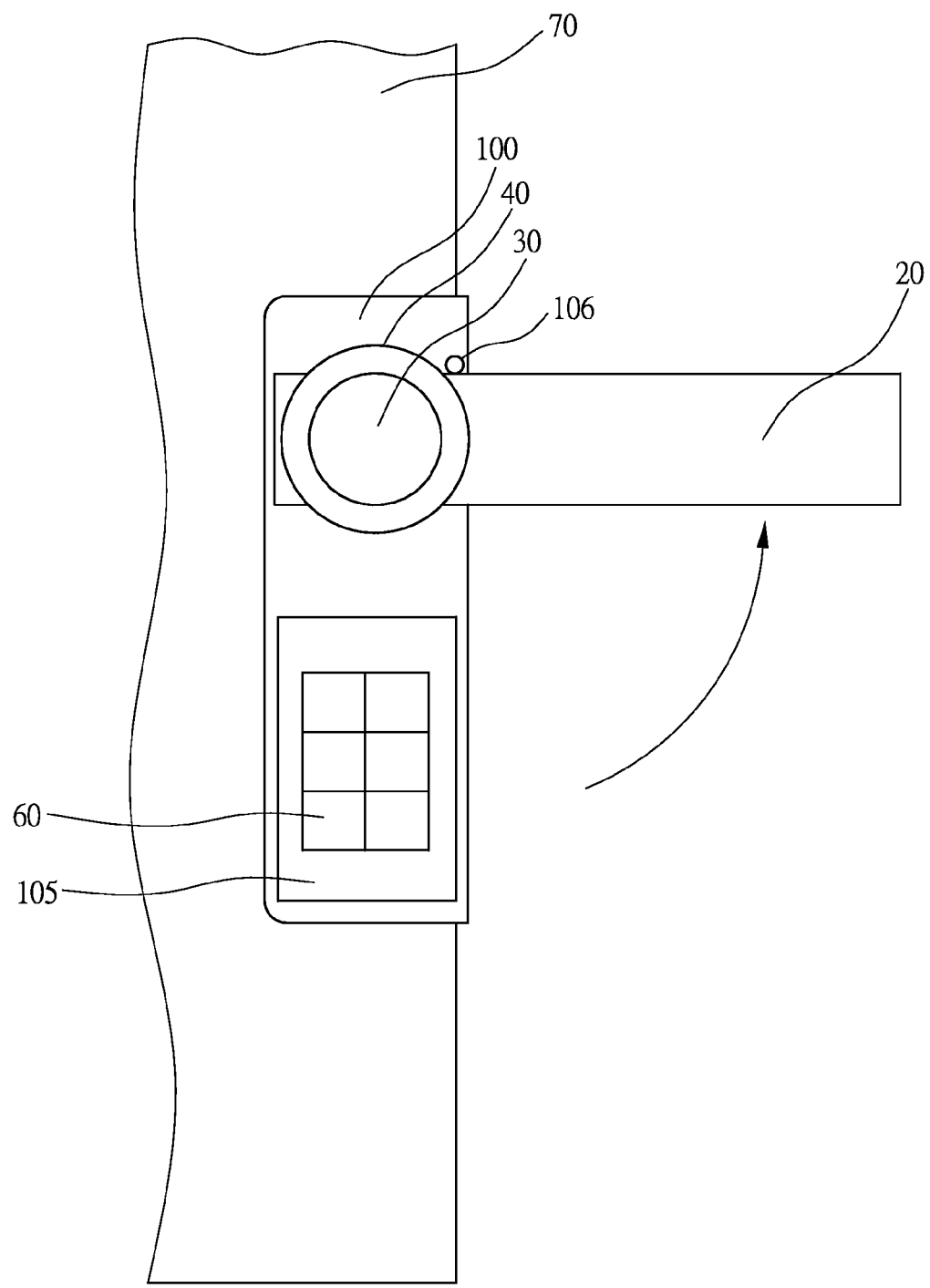
FIG. 6 is an operating schematic view of the height measurement device according to the third embodiment of the present invention.

FIG. 6 is a schematic view showing a use of the height measurement device according to the third embodiment of the present invention. With reference to the drawings and in particular to FIG. 6, the present invention is a height measurement device, which comprises a body 1 and a measurement unit 40. The body 1 comprises a clamping member 10, a height indicator 20, a pivot member 30, and a record list 60, wherein the clamping member 10 is composed of a first side wall 100, a second side wall 101 and a thirty side wall 102 and forms a clamping slit 103 thereof. The first side wall 100 has a first joint portion 104 and a side wall positioning element. The height indicator 20 has a first pivot portion 201, and the pivot member 30 is pivot jointed to the height indicator 20 on the first side wall 100 and comprises an adjacent portion 301, a second pivot portion 302 and a second joint portion 303. The second pivot portion 302 is jointed to the adjacent portion 301 with one end, and the other end of the second pivot portion 302 is jointed to the second joint portion 303. The second pivot portion 302 is pivot jointed to the first pivot portion 201, and the second joint portion 303 is moveable jointed to the first joint portion 104, while the pivot member 30 moves to a packing position, the adjacent portion 301 abuts the height indicator 20 whereby the height indicator 20 and the clamping member 10 are packed by the adjacent portion 301 (please refer to FIG. 2 and FIG. 3) The measurement unit 40 (the measurement unit 40 is a graduation measurement unit in this embodiment, such as a measuring tape; is disposed on the body.

The present invention is a height measurement device which further comprises two gaskets 50, one of the gaskets 50 is disposed between the clamping member 10 and the height indicator 20, and the other one is disposed between the height indicator 20 and the adjacent portion 301. The clamping member 10 further comprises a second accommodating portion 105 on the first side wall 100, and the record list 60 is demountable in the second accommodating portion 105.

FIG. 6 is a operating schematic view of the height measurement device according to the third embodiment of the present invention. With reference to the drawings and in particular to FIG. 6, the present invention is a height measurement device. First, the user takes the clamping member 10 to clamp a door plank 70, and turns the height indicator 20 to attach the side wall positioning element 106 of the first side wall 100, and the height indicator 20 is perpendicular to the second side wall 101 and positioned by the side wall positioning element 106. Then, the user adjusts the clamping member 10 moves up and down on along the door plank 70. The user locks the pivot member 30 when the height indicator 20 abuts the top of the user's head and rotates the pivot member 30 to a packing position, and the adjacent portion 301 abuts the height indicator 20 whereby the height indicator 20 and the clamping member 10 are packed by the adjacent portion 30. Finally, the graduation tool of the measurement unit 40 is drawn to the floor for measuring the height exactly, and the record list 60 is put in the accommodating portion 105 of the first side wall 100 to record the value of height every time.

Figure 7:
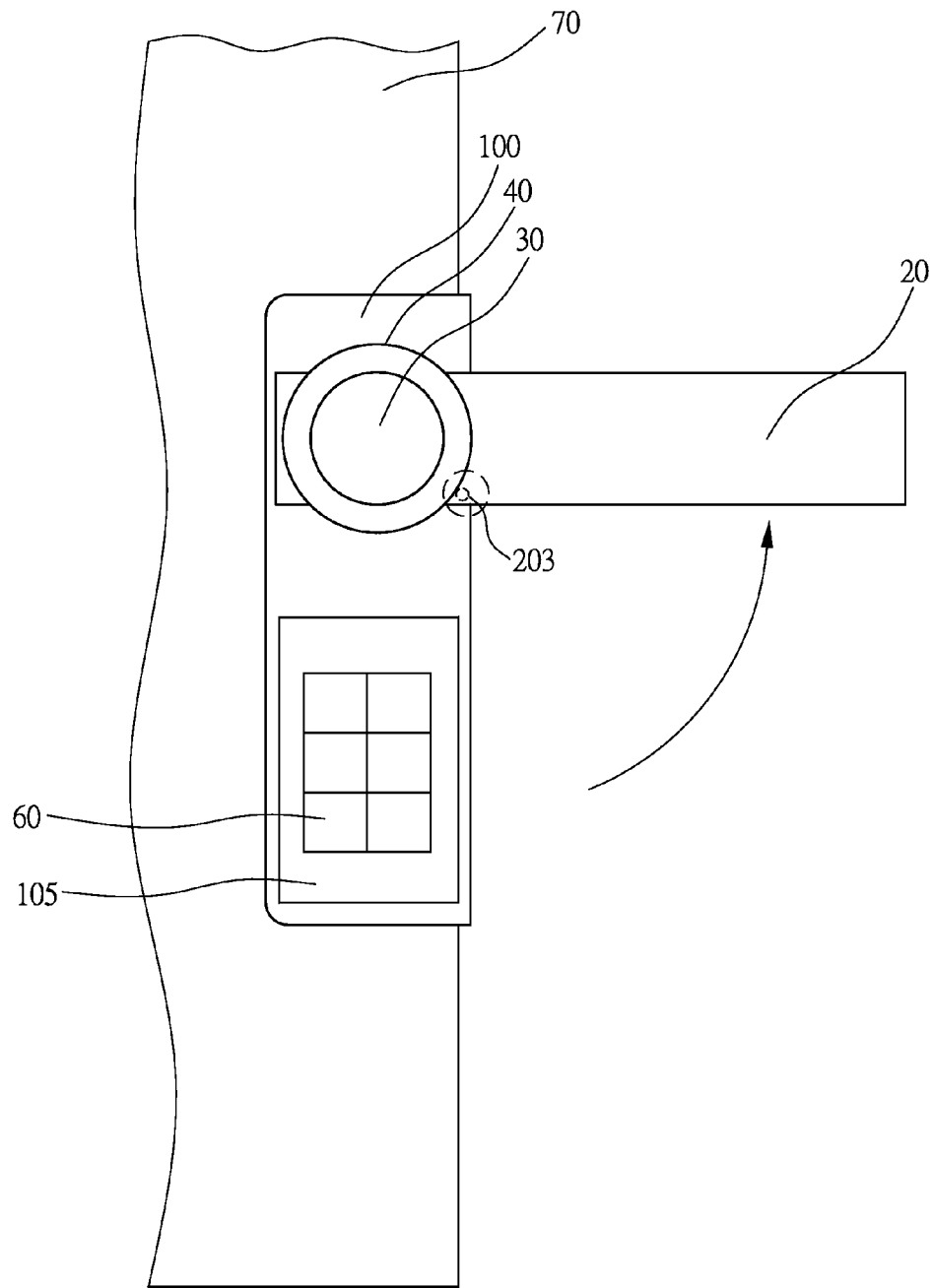
FIG. 7 is a operating schematic view of the height measurement device according to the fourth embodiment of the present invention.
Figure 8:
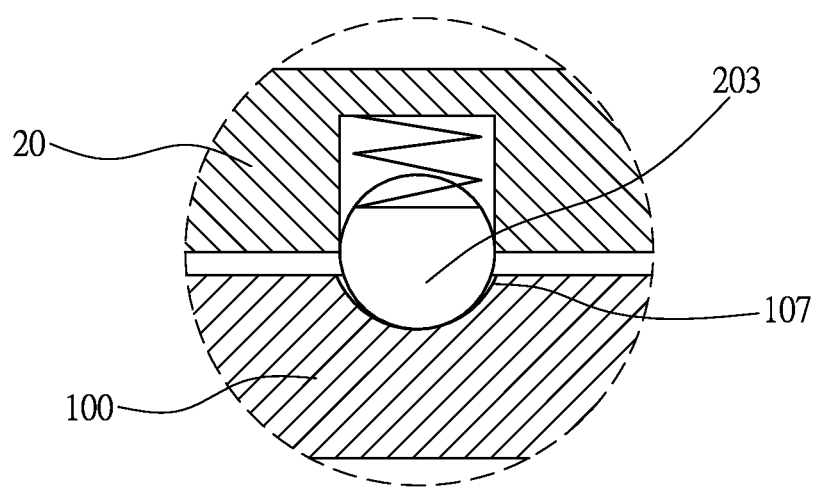
FIG. 8 is a enlarge view of the height measurement device according to the dotted line of FIG. 7.

FIG. 7 is a operating schematic view of the height measurement device according to the fourth embodiment of the present invention; FIG. 8 is a enlarge view of the height measurement device according to the dotted line of FIG. 7. With reference to the drawings and in particular to FIG. 7, the present invention is a height measurement device, which comprises a body 1 and a measurement unit 40. The body 1 comprises a clamping member 10, a height indicator 20, a pivot member 30, and a record 60, wherein the clamping member 10 is composed of a first side wall 100, a second side wall 101 and a thirty side wall 102 and forms a clamping slit 103 thereof. The first side wall 100 has a first joint portion 104, and the height indicator 20 has a first pivot portion 201. The pivot member 30 is pivot jointed to the, height indicator 20 on the first side wall 100 and comprises an adjacent portion 301, a second pivot portion 302 and a second joint portion 303. The second pivot portion 302 is jointed to the adjacent portion 301 with one end, and the other end of the second pivot portion 302 is jointed to the second joint portion 303, the second pivot portion 302 is pivot jointed to the first pivot portion 201, and the second joint portion 303 is moveable jointed to the first joint portion 104. While the pivot member 30 moves to a packing position, the adjacent portion 301 abuts the height indicator 20 whereby the height indicator 20 and the clamping member 10 are packed by the adjacent portion 301 (please refer to FIG. 2 and FIG. 3) The measurement unit 40 (the measurement unit 40 is a graduation measurement unit in this embodiment, such as a measuring tape) is disposed on the body.

The present invention is a height measurement device which further comprises two gaskets 50, one of the two gaskets 50 is disposed between the clamping member 10 and the height indicator 20, and the other one is disposed between the height indicator 20 and the adjacent portion 301. The clamping member 10 further comprises a second accommodating portion 105 on the first side wall 100, and the record 60 is demountable in the second accommodating portion 105. The height indicator 20 further comprises a first positioning element 203, and the first side wall 100 further comprises a second positioning element 107, while the height indicator 20 is perpendicular to the second side wall 102, the first positioning element 203 correspondingly joints to the second positioning element 107 (please refer to FIG. 8).

FIG. 7 is a operating schematic view of the height measurement device according to the fourth embodiment of the present invention. With reference to the drawings and in particular to FIG. 7, the present invention is a height measurement device. First, the user takes the clamping member 10 to clamp a door plank 70 and turns the height indicator 20 perpendicular to the second side wall 102, the first positioning element 203 correspondingly joints to the second positioning element 107 simultaneously (please refer to FIG. 8) Then, the user adjusts the clamping member 10 to move up and down along the door plank 70. The user locks the pivot member 30 when the height indicator 20 abuts the top of the user's head and the pivot member 30 moves to a packing position, the adjacent portion 301 abuts the height indicator 20 whereby the height indicator 20 and the clamping member 10 are packed by the adjacent portion 30. Finally, the graduation tool of the measurement unit 40 is drawn to the floor for measuring the height exactly, and the record list 60 is put in the accommodating portion 105 of the first side wall 100 to record the height value every time.

Figure 9:
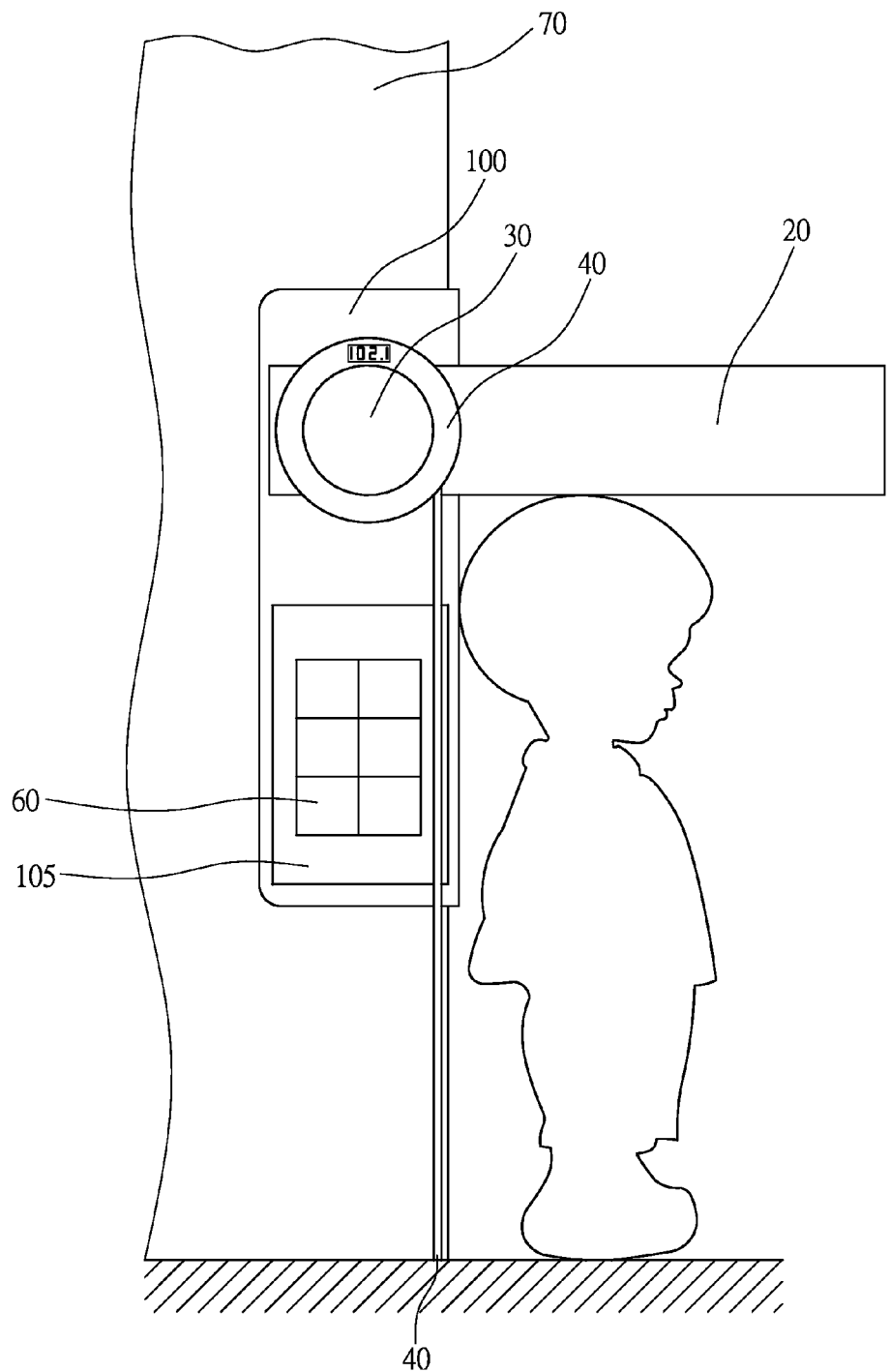
FIG. 9 is an operating schematic view of the height measurement device according to the fifth embodiment of the present invention.

FIG. 9 is a operating schematic view of the height measurement device according to the fifth embodiment of the present invention. With reference to the drawings and in particular to FIG. 9, the operation of the second embodiment as same as the first embodiment. However, the measurement unit 40 is an electronic measurement unit in fifth embodiment, such as electronic measuring tape. When the electronic measuring tape is drawn to the floor, the panel of the electronic measuring tape displays the current height for measuring the height exactly.

Figure 10:
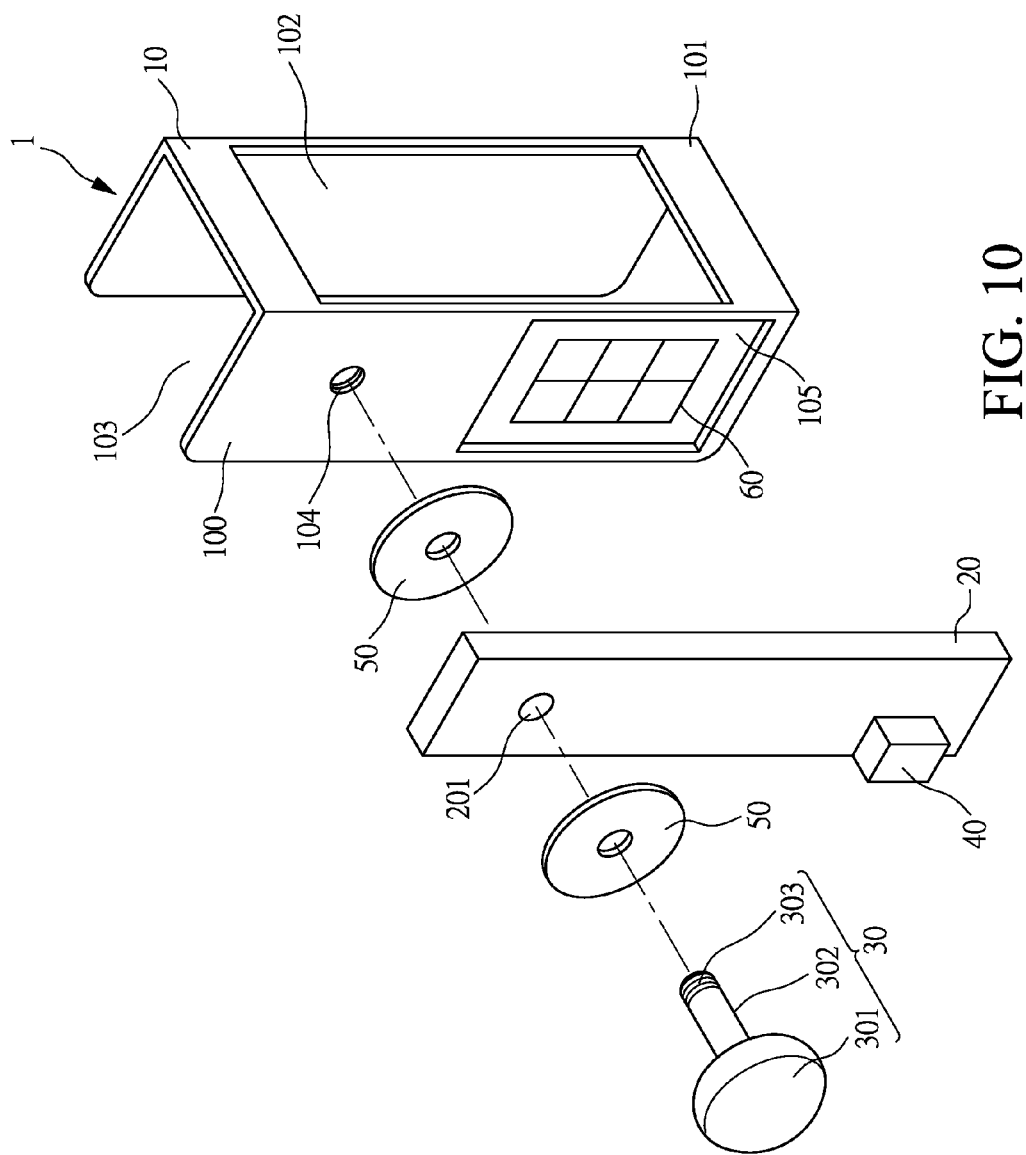
FIG. 10 is an exploded view of the height measurement device according to the sixth embodiment of the present invention.
Figure 11:
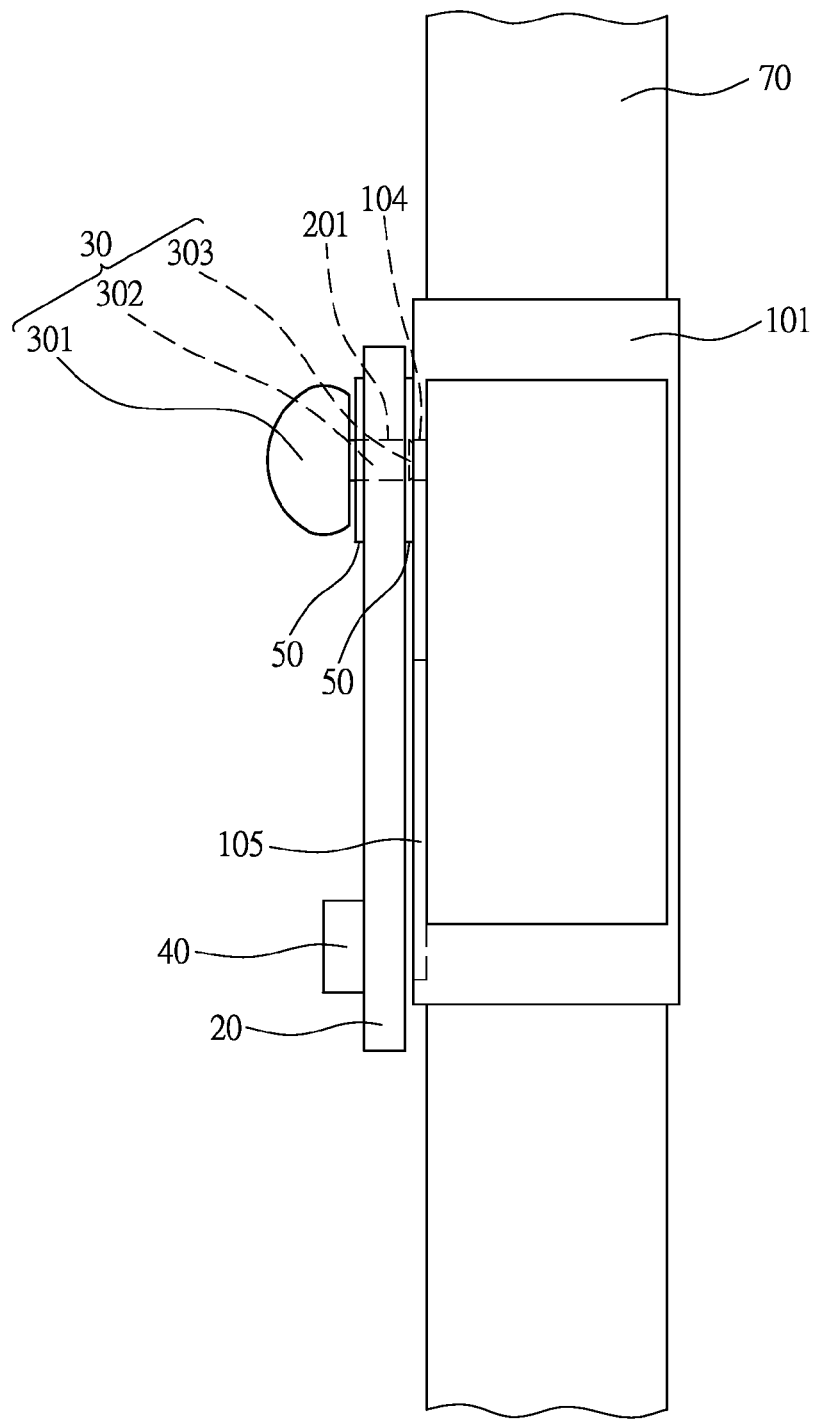
FIG. 11 is a cross-sectional view of the height measurement device according to the sixth embodiment of the present invention.
Figure 12:
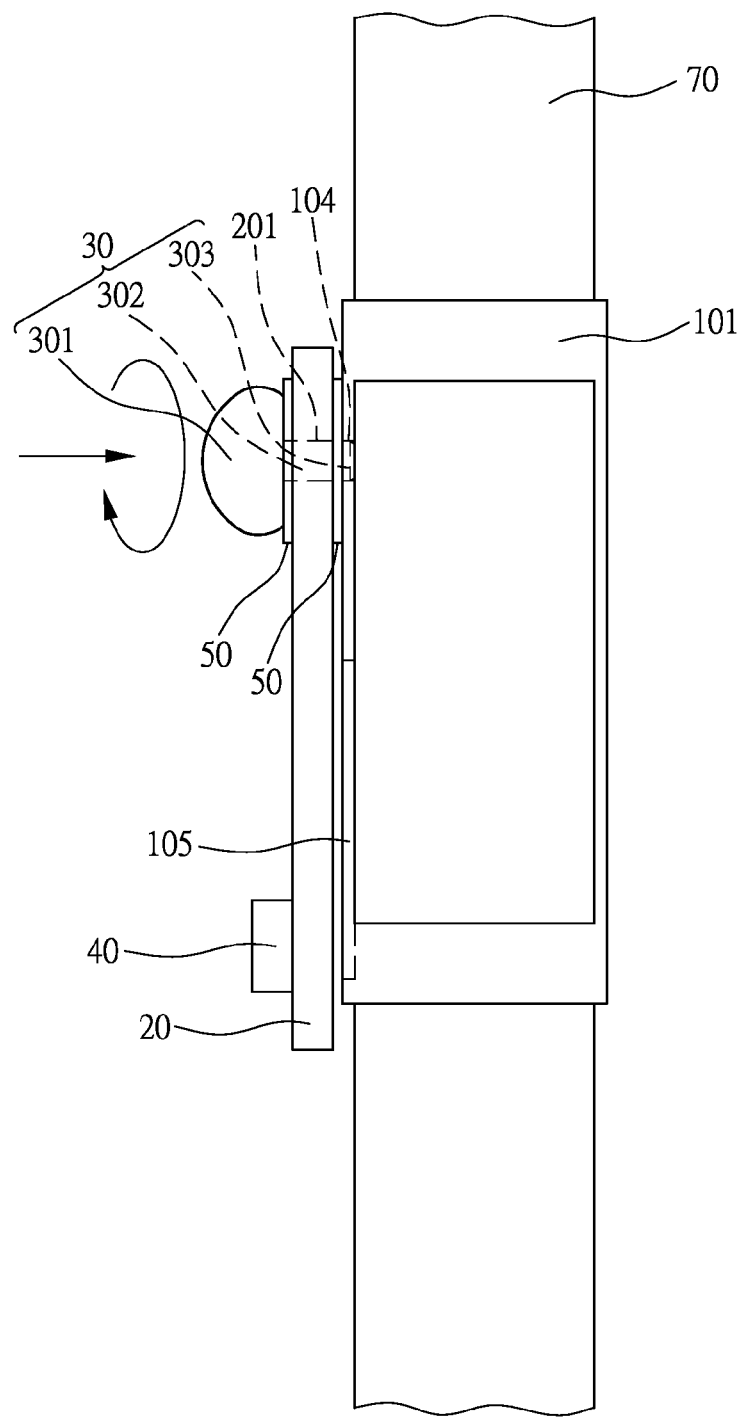
FIG. 12 is a cross-sectional view of the height measurement device according to the sixth embodiment of the present invention.

FIG. 10 is an exploded view of the height measurement device according to the sixth embodiment of the present invention; FIG. 11 is a cross-sectional view of the height measurement device according to the sixth embodiment of the present invention; FIG. 12 is a cross-sectional view of the height measurement device according to the sixth embodiment of the present invention. With reference to the drawings and in particular to FIG. 10, the present invention is a height measurement device, which comprises a body 1 and a measurement unit 40. The body 1 comprises a clamping member 10, a height indicator 20, a pivot member 30, and a record 60, wherein the clamping member 10 is composed of a first side wall 100, a second side wall 101 and a thirty side wall 102 and forming a clamping slit 103 thereof. The first side wall 100 has a first joint portion 104, the height indicator 20 has a first pivot portion 201, and the pivot member 30 is pivot jointed to the height indicator 20 on the first side wall 100 and comprises an adjacent portion 301, a second pivot portion 302 and a second joint portion 303. The second pivot portion 302 is jointed to the adjacent portion 301 with one end, and the other end of the second pivot portion 302 is jointed to the second joint portion 303. The second pivot portion 302 is pivot jointed to the first pivot portion 201, and the second joint portion 303 is moveable jointed to the first joint portion 104, while the pivot member 30 moves to a packing position, the adjacent portion 301 abuts the height indicator 20 whereby the height indicator 20 and the clamping member 10 are packed by the adjacent portion 301 (please refer to FIG. 11 and FIG. 12). The measurement unit 40 (the measurement unit 40 is a laser measurement unit in this embodiment) is disposed on the body.

The present invention is a height measurement device which further comprises two gaskets 50, one of the gaskets 50 is disposed between the clamping member 10 and the height indicator 20, and the other one is disposed between the height indicator 20 and the adjacent portion 301. The clamping member 10 further comprises a second accommodating portion 105 on the first side wall 100, and the record list 60 is demountable in the second accommodating portion 105.

Figure 13:
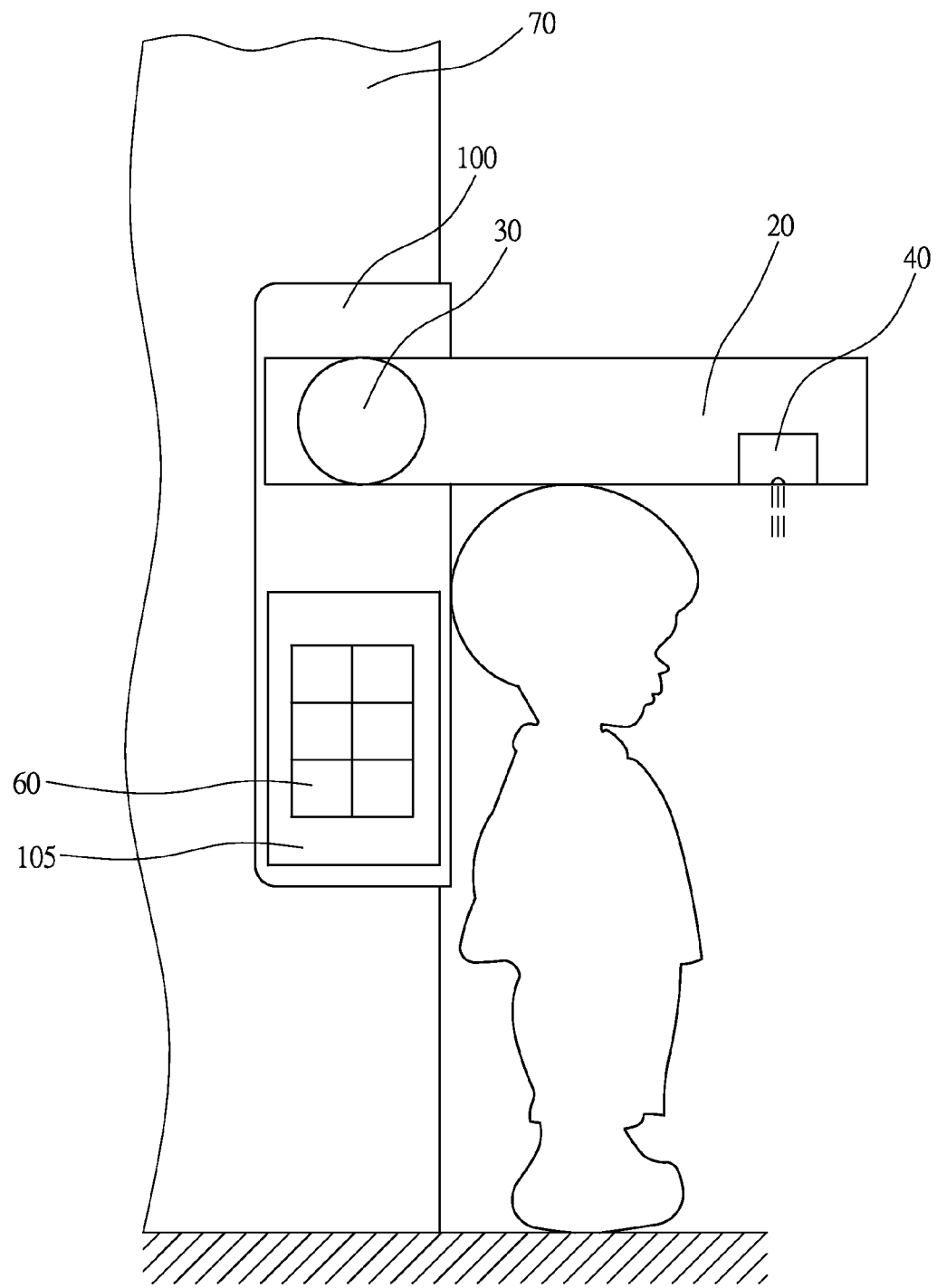
FIG. 13 is an operating schematic view of the height measurement device according to the sixth embodiment of the present invention.

FIG. 13 is a operating schematic view of the height measurement device according to the sixth embodiment of the present invention. With reference to the drawings and in particular to FIG. 13, the present invention is a height measurement device. First, the user takes the clamping member 10 to clamp a door plank 70, and turns the height indicator 20 to a horizontal position, and the height indicator 20 is perpendicular to the second side wall 101. Then, the user adjusts the clamping member 10 to move up and down along the door plank 70. The user locks the pivot member 30 when the height indicator 20 abuts the top of the user's head and the pivot member 30 moves to a packing position, the adjacent portion 301 abuts the height indicator 20 whereby the height indicator 20 and the clamping member 10 are packed by the adjacent portion 30. Finally, the user turns on the laser measurement unit to emit, a light, and measures the height from the soles of the user's feet to the top of the user's head according to the light reflected to the laser measurement unit. The record list 60 is put in accommodating portion 105 of the first side wall 100 to record the height value every time.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A height measurement device, detachably disposed on an article, comprising:
   a body, comprising: a clamping member, having a first joint portion and a clamping slit, wherein the clamping slit is composed of a first side wall, a second side wall and a third side wall, and is configured to clamp the article,
   wherein the first side wall comprises a side wall positioning element disposed thereon, while the height indicator abuts the side wall positioning element, the height indicator is fixed at the measurement position which is perpendicular to the second side wall,
   wherein the height indicator further comprises a first positioning element, and the first side wall further comprising a second positioning element, while the height indicator is perpendicular to the second side wall, the first positioning element correspondingly joints the second positioning element;
   a height indicator, having a first pivot portion; and
   a pivot member, having an adjacent portion and a second joint portion, and pivotally jointing the height indicator to the clamping member through the first pivot portion, whereas the pivot member is moved to allow the second joint portion joint to the first joint portion, the adjacent portion abuts the height indicator onto the clamping member so as to fix the height indicator at a measurement position; and
   a measurement unit, disposed on the body, for use in measuring a height of the measurement position.

2. The height measurement device as claimed in claim 1 further comprising two gaskets, one of the two gaskets is disposed between the clamping member and the height indicator, and the other gasket is disposed between the height indicator and the adjacent portion.

3. The height measurement device as claimed in claim 1, wherein the height indicator further comprises a first accommodating portion and the measurement unit is detachable disposed in the first accommodating portion.

4. The height measurement device as claimed in claim 1, wherein the measurement unit is an optics measurement.

5. The height measurement device as claimed in claim 1, wherein the measurement unit is a graduation measurement unit, and is disposed between the adjacent portion and the height indicator.

6. The height measurement device as claimed in claim 1, wherein the measurement unit is an electronic measurement unit, and is disposed between the adjacent portion and the height indicator.

7. The height measurement device as claimed in claim 1, further comprising a record list, demountable disposed in the clamping member, for use in recording the height of the measurement position.

* * * * *